United States Patent [19]

Gross

[11] Patent Number: 5,372,254
[45] Date of Patent: Dec. 13, 1994

[54] CATHETER PACKAGE AND DELIVERY SYSTEM

[75] Inventor: James R. Gross, Wareham, Mass.

[73] Assignee: The Kendall Company, Mansfield, Mass.

[21] Appl. No.: 186,954

[22] Filed: Jan. 27, 1994

[51] Int. Cl.$^5$ ............................................. B65D 85/30
[52] U.S. Cl. ................................. 206/364; 206/488
[58] Field of Search ........................ 206/363–366, 206/368, 388, 486–489

[56] References Cited

U.S. PATENT DOCUMENTS

| | | | |
|---|---|---|---|
| 2,947,415 | 8/1960 | Garth | 206/364 |
| 3,926,309 | 12/1975 | Center | 206/364 |
| 3,934,721 | 1/1976 | Juster et al. | 206/364 |
| 4,262,800 | 4/1981 | Nethercutt | 206/364 |
| 4,332,322 | 6/1982 | Jaeschke et al. | 206/364 |
| 4,379,506 | 4/1983 | Davidson | 206/364 |
| 5,131,537 | 7/1992 | Gonzales | 206/364 |
| 5,165,540 | 11/1992 | Forney | 206/364 |
| 5,226,530 | 7/1993 | Golden | 206/364 |
| 5,226,535 | 7/1993 | Rosdhy et al. | 206/364 |
| 5,322,163 | 6/1994 | Foos | 206/364 |

*Primary Examiner*—Jimmy G. Foster
*Attorney, Agent, or Firm*—Alvin Isaacs

[57] ABSTRACT

Disclosed is a catheter package and delivery system which is directed to the problem of the catheter, or any position of it, inadvertently tumbling out on withdrawal from its package for use and accidentally contacting a nonsterile surface. The catheter is packaged in a coiled manner such that the distal tip is removable through a first hole in the package and the catheter may then be uncoiled and ultimately removed through a second hole in the package as the catheter is threaded through a needle for introduction into the patient.

5 Claims, 1 Drawing Sheet

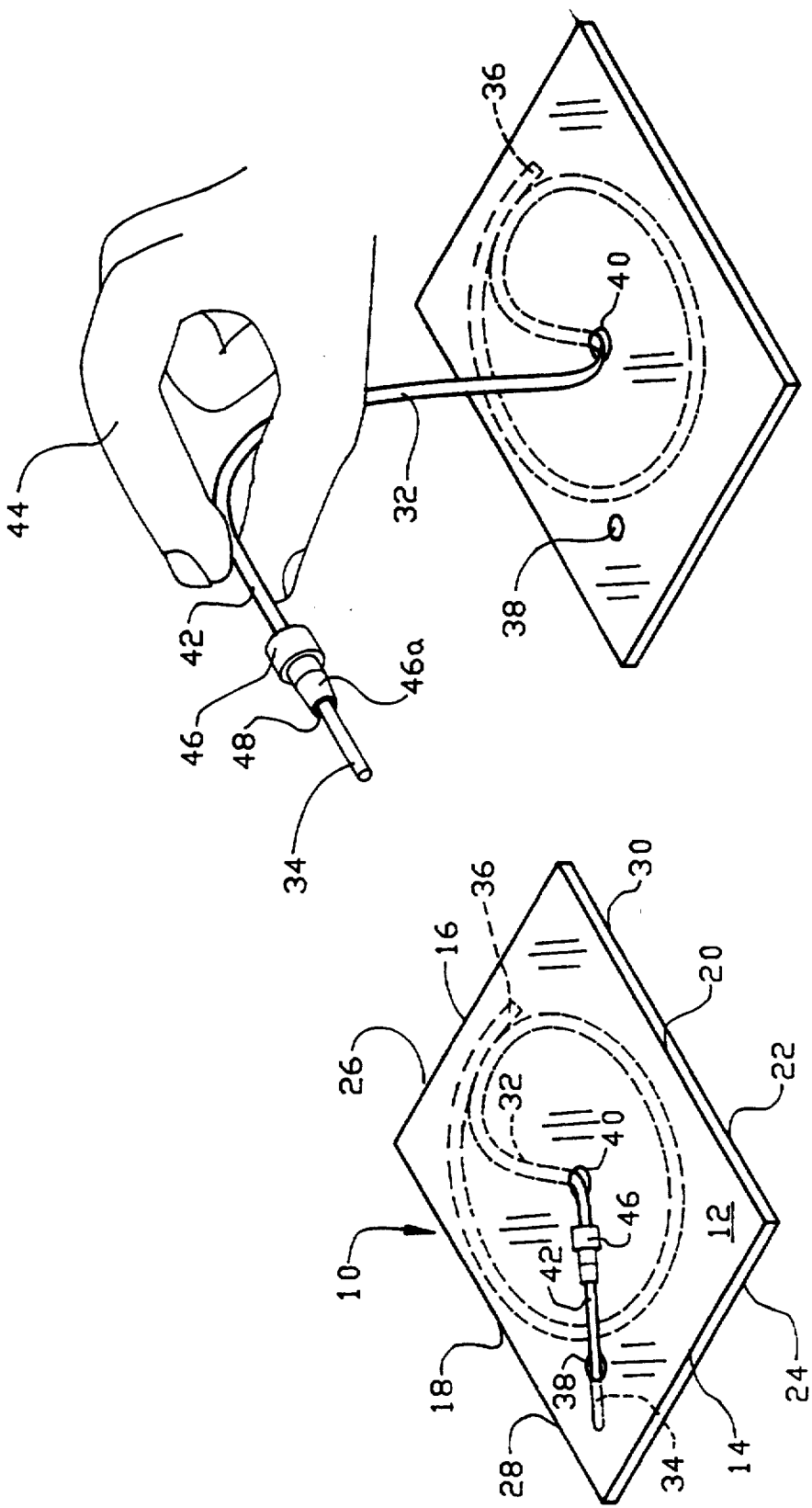

CATHETER PACKAGE AND DELIVERY SYSTEM

BACKGROUND OF THE INVENTION

Currently, epidural catheters are provided to the anesthesiologist inside a bag made of polyethylene or other polymeric material. The bag is sealed around the four edges and a perforation is provided on one edge to facilitate opening for removal of the catheter.

Upon removal from the bag, the entire catheter falls out. Consequently, the anesthesiologist must be careful to assure that the catheter, typically on the order of three feet in length, or any portion of it, does not contact a nonsterile surface.

Accordingly, it will be appreciated that there is a great need in the art for a packaging system for catheters such as those used for anesthesiology which will deliver the sterile catheter into the hands of the clinician in a fail-safe manner obviating the aforementioned problems.

Stated simply, the task of this invention is to devise a packaging and delivery system for delivering the catheter from its sterile package to the anesthesiologist or other clinician in a manner which avoids unwanted inadvertent contact with nonsterile surfaces in the course of unpackaging it in preparation for a medical or surgical procedure.

BRIEF DESCRIPTION OF THE INVENTION

In accordance with this invention the task is solved in an elegant and cost-effective manner by packaging the catheter coiled within a plastic bag in such a way that the catheter uncoils and is removed from the bag as the distal end of the catheter is advanced through a needle into the body for initiating the medical or surgical procedure.

BRIEF DESCRIPTION OF THE DRAWINGS

FIG. 1 is a perspective view of the catheter packaging and delivery system of this invention; and FIG. 2 is a similar view showing the manner of its removal from the bag in which it is packaged.

DETAILED DESCRIPTION OF THE INVENTION

As heretofore mentioned, the present invention is directed to a novel packaging and delivery system for catheters which obviates the inadvertent contact of the catheter with a non-sterile substrate on removing the catheter form its package, which contact necessitates obtaining another sterile catheter which possibly entails opening a new surgical tray including the catheter package as a component part thereof.

While the invention is directed to the various catheters introduced through a needle into the body, it is particularly directed to epidural catheters and the invention will be described in detail hereinafter by reference thereto.

For a full understanding of the nature and objects of the invention, reference should be had to the following detailed description taken in conjunction with he accompanying drawing.

As shown in the drawing, the catheter package and delivery system comprises a bag 10 of a flexible preferably transparent material such as polyethylene consisting of a top sheet 12 having opposed ends 14,16 and opposed edges 18,20 joining the ends 14,16; and a bottom sheet 22 having opposed ends 24,26 and opposed edges 28,30 joining the ends 24,26.

The sheets 12 and 22 are sealed around their periphery in superposed relationship, e.g. by heat-sealing, to enclose catheter 32 having a distal end 34 and a proximal end 36.

Sheet 12 has a pair of holes or openings 38,40 spaced apart such that the distal end 34 of the catheter is encased within the bag through opening 38, a portion 42 of the catheter is located outside the bag for gripping and the remainder of the catheter between portion 42 and proximal end 36 is packaged in a coiled position within bag 10 so as to be removable through hole 40. While not critical to the practice of the invention the holes 38,40 may be spaced apart on the order of, say 1.5–3 centimeters on center, a typical example being on the order of about 2cms.

While not critical and accordingly per se no part of this invention, the catheter 32 will typically have a threading assist device 46 having a leading or distal end 46a and a trailing or proximal end (not clearly shown) with a hollow bore having an internal diameter greater than the external diameter extending between the ends of the threading assist device so that the device is easily movable along the length of the catheter.

In operation, the catheter package is removed from the procedural tray or other sterile environment in preparation for the medical/surgical procedure. The catheter portion 42 outside package 10 and/or device 46 is then grasped with the fingers 44 to remove the distal end 34 of the catheter from within hole 38 (as seen in FIG. 2. With the aid of the thread assist device 46 preventing kinking, the catheter is then threaded, distal end first, into the needle for introduction of the catheter into the body, e.g. into the epidural space for administering anesthesia to the patient.

As will be appreciated, as the distal end of the catheter is threaded through the needle outside the bag, the portion of the catheter initially contained within the bag slowly unwinds as it is pulled through hole 40 until the entire catheter is free from bag 10.

It will also be appreciated that during this procedure for removing the catheter from its container and threading it through the needle, inadvertent contact with nonsterile substrates is readily avoided without requiring the exercise of manual dexterity, thereby solving the task of the invention in a simple but elegant manner.

Since certain changes may be made without departing from the scope of the invention herein contemplated, it is to be expressly understood that the foregoing description and accompanying drawing is to be taken as being illustrative and not in a limiting sense.

What is claimed is:

1. A package and delivery system for a catheter to be introduced into a patient through a needle, comprising:

a plastic bag sealed around its periphery to define a closure for a catheter having opposed distal and proximal ends contained within the bag;

the bag having first and second spaced openings on one surface thereof;

the distal end of the catheter being inserted within the first opening, the portion of the catheter extending from the first opening to the second opening being disposed outside the bag and the remaining portion of the catheter being disposed within the bag through the second opening, whereby on removal of the distal end of the catheter from within the first opening and then threading it through the needle, the catheter is pulled from within the bag through the second opening.

2. A package and delivery system as defined in claim 1 wherein the catheter is coiled within the bag for easy unwinding on threading through the needle.

3. A package and delivery system as defined in claim 1 wherein the catheter is an epidural catheter.

4. A package and delivery system as defined in claim 1 wherein the bag comprises a flexible transparent material.

5. A package as defined in claim 1 wherein the first and second openings are spaced apart on the order of from about 1.5 to about 3.0 centimeters.

* * * * *